(12) United States Patent
Babes-Dornea et al.

(10) Patent No.: US 7,582,196 B2
(45) Date of Patent: Sep. 1, 2009

(54) LAMINATED MEMBRANES FOR DIFFUSION LIMITED GAS SENSORS RESISTANT TO PRESSURE VARIATIONS

(75) Inventors: Elena Babes-Dornea, Pierrefonds (CA); Yves Grincourt, Ottawa (CA); Claude Beauchemin, Valleyfield (CA)

(73) Assignee: General Electric Company, Schenectady, NY (US)

( * ) Notice: Subject to any disclaimer, the term of this patent is extended or adjusted under 35 U.S.C. 154(b) by 853 days.

(21) Appl. No.: 10/918,692

(22) Filed: Aug. 16, 2004

(65) Prior Publication Data

US 2006/0032742 A1 Feb. 16, 2006

(51) Int. Cl.
*H01M 8/00* (2006.01)
(52) U.S. Cl. .................. 204/400; 204/431; 204/421; 204/406; 204/427; 205/781; 205/783.5
(58) Field of Classification Search .......... 204/431, 204/421, 406, 427; 205/781, 783.5
See application file for complete search history.

(56) References Cited

U.S. PATENT DOCUMENTS

| | | | |
|---|---|---|---|
| 4,271,474 A | 6/1981 | Belanger et al. | |
| 4,293,399 A | 10/1981 | Belanger et al. | |
| 4,463,593 A * | 8/1984 | Parker | 73/19.05 |
| 4,564,359 A * | 1/1986 | Ruhland | 604/6.09 |
| 4,695,361 A * | 9/1987 | Grady | 204/415 |
| 6,436,257 B1 * | 8/2002 | Babas-Dornea et al. | 204/415 |
| 6,506,296 B2 | 1/2003 | Babes-Dornea et al. | |
| 2001/0032789 A1 * | 10/2001 | Babes-Dornea et al. | 205/775 |
| 2005/0086998 A1 | 4/2005 | Qin | |

FOREIGN PATENT DOCUMENTS

CN 200310111953.7 10/2003

OTHER PUBLICATIONS

Submission of Protest by attorney Raymond Y. Chan (Feb. 14, 2008). Protest Letter included with the Submission of Protest.

* cited by examiner

*Primary Examiner*—Mark F Huff
*Assistant Examiner*—Rashid Alam
(74) *Attorney, Agent, or Firm*—Nixon & Vanderhye P.C.

(57) ABSTRACT

A micro fuel cell sensor having laminated gas permeable membrane. The sensor comprises a housing, first and second gas diffusing electrodes spaced from one another, a fuel-cell spacer having an acidic electrolyte disposed between said first and second electrodes, and two gas permeable membranes. The first gas permeable membrane comprises a polymer laminated on a metal substrate, wherein the substrate comprises pores that have dimensions at least less than one-half the thickness of the polymer film.

20 Claims, 4 Drawing Sheets

LAMINATED MEMBRANES FOR DIFFUSION LIMITED GAS SENSORS RESISTANT TO PRESSURE VARIATIONS

BACKGROUND OF THE INVENTION

This invention relates to a sensor with a laminated membrane that analyzes gasses dissolved in dielectric oil. In particular, this invention relates to a sensor that measures dissolved hydrogen with a laminated membrane that is resistant to pressure variations over the normal use of the sensor in, for example, electric transformers. This invention also relates to an apparatus that contains the sensor that measures dissolved gasses.

An apparatus for measuring hydrogen content and partial hydrogen pressure in gas streams is disclosed in U.S. Pat. No. 6,506,296 to Babes-Dornea. Other methods of measuring hydrogen dissolved in liquids are disclosed in U.S. Pat. No. 4,271,474 and U.S. Pat. No. 4,293,399 to Belanger. The use of micro fuel cell sensors to measure dissolved gasses in oil is well know in the art. Typically, a micro fuel cell comprises two electrodes separated by an electrolyte. These devices also contain polymer membranes that allow dissolved gasses to permeate through, but not the oil the gasses are dissolved in. The polymer membranes contained in these devices are very sensitive, as they vary in thickness from only about 25 to about 250 microns (1 and 10 mils).

Standard micro fuel cell sensors, as typically used in the industry, are attached to devices that contain dielectric oil, like an electric transformer. Over the normal course of operation, these sensors see wide changes in temperature and pressure. These variations in temperature and pressure can cause damage to these polymer membranes. In order to overcome the high-pressure effects, the circular shape polymeric membrane can be supported by a porous metallic disc. The sensors with supported membranes can withstand positive pressures up to about 10.3 MPa or 1500 psi without significant damage to the membrane.

The membranes supported inside the sensor are protected against the positive pressure applied, while remaining vulnerable to negative pressures (vacuum), created when the outside pressure becomes smaller than the pressure inside the sensor. The negative pressure situations create stresses on the membranes that cause them to rupture. Once the membrane is ruptured, the sensor becomes "flooded" with dielectric oil, which causes the sensor to fail. These vacuum occurrences, which account for ~80% of sensor failures during field operations, usually arise during transformer maintenance. Further, temperature variations during operation cause thermal expansion and contraction of the thin membranes that affect their permeability and thus, sensor reliability. The membrane side facing the oil can't be protected with a porous disc (outside the detector) because the porous structure would be soaked with oil, further hindering the gas circulation towards the membrane.

Therefore, a need exists for a polymer membrane that allows the sensor to be serviced and utilized over normal operations and maintains reliability and prevents failure. Finally, a further need exists to develop an apparatus that contains the micro fuel cell sensor that will measure the dissolved gasses in dielectric oil.

BRIEF DESCRIPTION OF THE INVENTION

Accordingly, a micro fuel cell sensor, as embodied by the invention, comprises a housing; a sensing element comprising first and second gas diffusing electrodes spaced from one another, said sensing element disposed in said housing; a fuel-cell spacer having an acidic electrolyte disposed between said first and second electrodes; a first gas permeable membrane, separating said first electrode from the oil with dissolved gas and enabling gas dissolved in oil to diffuse therethrough, said first membrane being spaced from said first electrode enabling gas diffused through said first membrane to contact said first electrode; a second gas permeable membrane separating said second electrode from atmospheric air and defining a second cavity therewith isolated from said first cavity.

Another aspect of the invention discloses a laminated gas permeable membrane. The membrane comprises polymer laminated on a metal disc and is impervious to oil. The gas permeation rate through the laminated membrane is less than the rate of the electrochemical gas sensing reaction occurring in the sensor. The polymer in the membrane comprises at least one of Polytetrafluoroethylene (PTFE), Perfluorinated Ethylene-Propylene Copolymer (FEP), Perfluoroalkoxy PTFE (PFA), Polyvinylidene fluoride (PVDF), Polyvinyl Chloride (PVC), Polyimide, Polyethylene (PE), Polyether Ester Ketone (PEEK), Polycarbonate (PC) and Polyurethane, and has a thickness that ranges from about 1 mil (25 micron) to about 10 mil (250 micron).

The gas permeable membrane further comprises a porous metal disc that supports the polymer film under positive and negative pressure. The porous metal disc further comprises at least one of stainless steel, high nickel and nickel-copper alloys, bronze, and titanium. The porous metal disc also comprises pores, wherein the dimension of the pores of the metal disc are less than or equal to about one-half of the polymer thickness. The dimension of the pores of the metal disc are much larger than the gas molecules to be analyzed by the sensor.

An apparatus for measuring dissolved gasses in oil, comprising a housing; a micro-fuel cell sensor disposed in said housing; a cover member; said sensor comprising: a sensing element comprising first and second gas diffusing electrodes spaced from one another, said sensing element disposed in said housing; a fuel-cell spacer having an acidic electrolyte disposed between said first and second electrodes; a first gas permeable membrane, separating said first electrode from the oil with dissolved gas and enabling gas dissolved in oil to diffuse there through, said first membrane being spaced from said first electrode enabling gas diffused through said first membrane to contact said first electrode; a second gas permeable membrane separating said second electrode from atmospheric air and defining a second cavity therewith isolated from said first cavity.

DETAILED DESCRIPTION OF THE INVENTION

Figure 1:
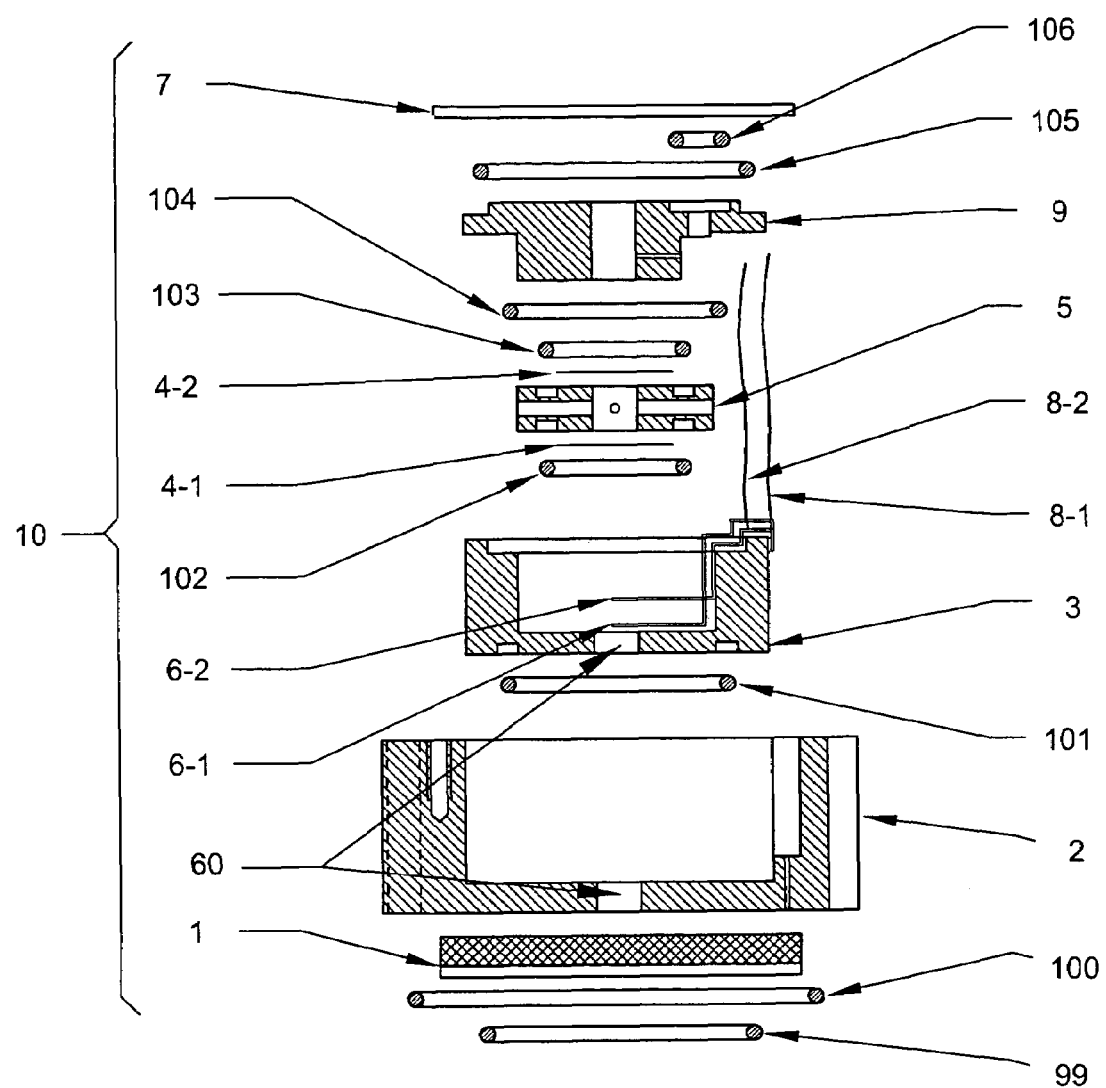
FIG. 1 is an exploded cross-sectional view of a micro-fuel cell sensor assembly.
Figure 2:
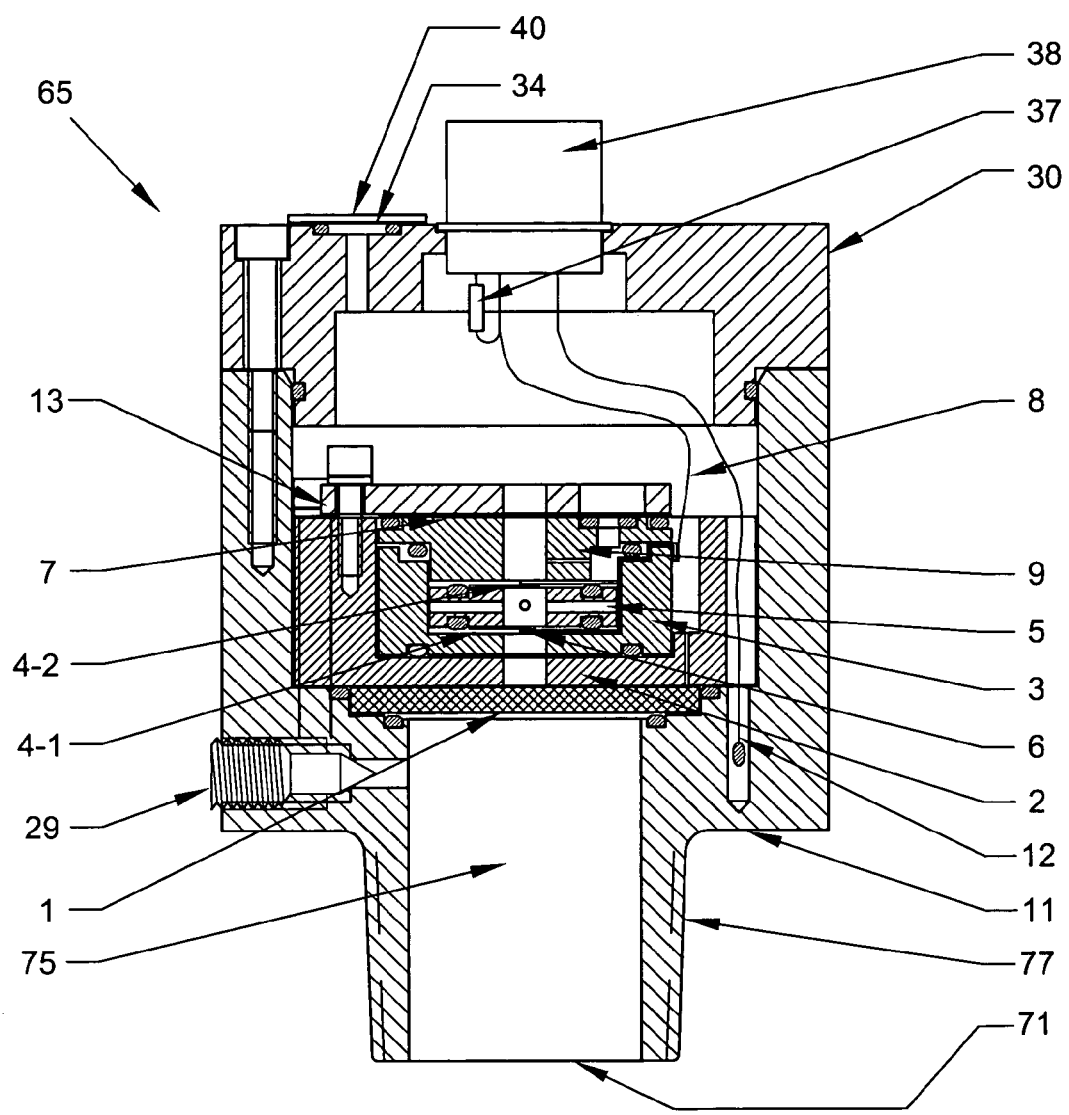
FIG. 2 is a cross-sectional view a micro-fuel cell sensor body, with cover assembly as shown in FIG. 3, for accommodating the micro-fuel cell sensor of FIG. 1.

Referring to FIGS. 1 and 2, these figures illustrate an example of a compact fuel cell sensor device 10 according to the present invention, for being connected to an aperture provided into one of the walls of a receptacle containing, for example, a dielectric fluid. In FIG. 1 there is illustrated a detailed exploded view of a micro-fuel cell sensor assembly 10 for measuring partial hydrogen pressure in dielectric oil. FIG. 2 illustrates a cross-section of an assembled sensor apparatus 65. The physical assembly of the sensor in this embodiment is similar as the gas sensors disclosed in Babes-Dornea '296 and '257. Although the exemplary embodiment is intended for measuring dissolved hydrogen in dielectric oil, this invention can also be utilized to measure other dissolved gasses in fluid systems other than the one presented herein.

The fuel cell sensor device 65 has a hollow probe base body 11 comprising a holding element 11 and a projection element 71. The holding element 11 has a socket opening for receiving other elements of the sensor such as the fuel cell element. The projection element 71 has central channel 75 therein and a threaded outer surface 77. As may be seen from FIG. 1, when the probe base body 65 is taken alone (i.e. viewed apart from the assembled sensor device) the socket opening and the central channel 75 communicate with each other. The fuel cell sensor device 65 has a gas extraction membrane 1 which has an incoming fluid side and a gas side; the gas extraction membrane 1 may be of polymeric material. The gas extraction membrane 1, hereinafter also referred to as a laminated membrane element or polymer laminated membrane, is thus disposed for contact on one side thereof with fluid (not shown) which may contain dissolved fault gasses such as hydrogen. O-ring seals 100 and 101 are disposed on respective sides of the gas extraction membrane 1 in order to provide a fluid tight seal about the gas extraction membrane 1. The gas extraction membrane 1 thus separates the central channel 75 and the socket opening so that during use when the central channel 75 is filled with fluid only a gas (such as hydrogen) may pass from the dielectric fluid side of the gas extraction membrane 1 to the other opposed default gas side thereof.

The sensor 10 as described above is adapted to be placed in a fuel cell sensor device 65 as illustrated in FIG. 2. The fuel cell sensor device 65 has a polymer laminated membrane element 1 and holder means defining an intermediate fuel cell cup 2. The intermediate fuel cell cup 2 is insertable into the socket opening. An external gas stream is received in the sensor body 11 through openings defined by apertures 60.

The intermediate fuel cell cup 2 has a bottom provided with an aperture 60. The polymer laminated membrane element 1 and the O-ring seals 99 and 100 are also insertable into the socket opening such that when the intermediate fuel cell cup 2 is fixed in place in the socket opening the polymer laminated membrane support element 1 and the O-ring seals 99 and 100 are held in place so as to provide the above mentioned fluid tight seal about the polymer laminated membrane 1. The intermediate fuel cell cup 2 is held in place to the holding element 11 by any appropriate means, such as, but not limited to, a plurality of socket screw and lock washer combinations, which are not shown.

The fuel cell sensor device 65 also has means defining an inner fuel cell cup 3 which is insertable in the intermediate fuel cell cup 2 as shown. The inner fuel cell cup 3 has a bottom also provided with an aperture 61. As may be seen the apertures in the bottom of the intermediate and inner fuel cell cups are aligned along the longitudinal axis of the fuel cell sensor device 65. An O-ring seal 101 is disposed between the bottom of the intermediate and inner fuel cell cups.

A fuel cell cover 9 is also provided for the inner fuel cell cup 3. The fuel cell cover 9 has a projection which is insertable into the inner fuel cell cup 3 as shown. The fuel cell cover 9 has a central opening and a smaller opening set to one side of the larger opening; the smaller opening facilitates the access of the oxygen containing gas to the fuel cell.

The fuel cell sensor device 65 has a fuel cell element. The fuel cell element has an annular or ring shaped support member 5 which defines a central electrolyte chamber which is filled with a suitable acidic gel electrolyte (e.g. a sulphuric acid gel). The electrode means of the fuel cell element consists of a first 4-1 and second 4-2 electrode. The first electrode means 4-1 is electrically connected by a Pt metal strip or foil 6-1 to a respective wire connector element or lead 8-1; likewise, the second electrode means 4-2 is electrically connected by a Pt metal strip (or foil) 6-2 to another respective wire connector element or lead 8-2; the wire connector elements are collectively designated by the reference numeral 8. The wire connector elements are electrically connected to a suitable fixed load resistance 37 (e.g. 500 to 2200 ohms).

The fuel cell sensor device 65 has an intermediate fuel cell cover plate 13 which is attached by any appropriate means, such as, but not limited to, a plurality of screw and lock washer combinations, not shown, to the intermediate fuel cell cup 2 so as to urge the projection into the inner fuel cell cup 3 as shown in FIG. 1 to maintain the fuel cell cover 9 and the inner fuel cell cup 3 in place. O-ring seals, 99 101, 102, 103, 104, 105, and 106 are also provided which provide for a fluid (i.e. gas tight) seal between respective adjacent elements when the intermediate fuel cell cover plate 13 is attached to the intermediate fuel cell cup 2 as shown in FIG. 2. A gas permeable polymer membrane 7 is also provided between the intermediate fuel cell cover 9 and the fuel cell cover plate 13 sealed with the O-ring seals 105 and 106.

The fuel cell sensor device 65 has a thermistor 12. The fuel cell sensor device 65 also has bleed means for bleeding fluid from the channel. The bleed means comprises a bleed screw 29 adapted to cooperate with a bleed opening to allow for such fluid bleeding. The bleed screw is utilized to normalize the air trapped inside the sensor 65 and the oil that displaces it during initial installation. After the initial installation, the bleed screw remains closed during normal operations. The bleed screw can be opened to allow samples of the monitored fluid stream to be taken.

As mentioned above an electronic measuring device (not shown) may be electrically connected to the load resistance 37 via the connector 38 so as to permit one to measure the intensity of the current generated by the oxido-reduction reactions occurring at the first and second electrode means. The electronic part of the measuring apparatus (not shown) may take any suitable (known) form i.e. the various electronic measure and display devices may be take on any suitable form. The signal generated by the electrochemical cell is essentially a current having an intensity proportional or in well defined correlation to the hydrogen content of the fluid (e.g. dielectric oil) sample.

Figure 3:
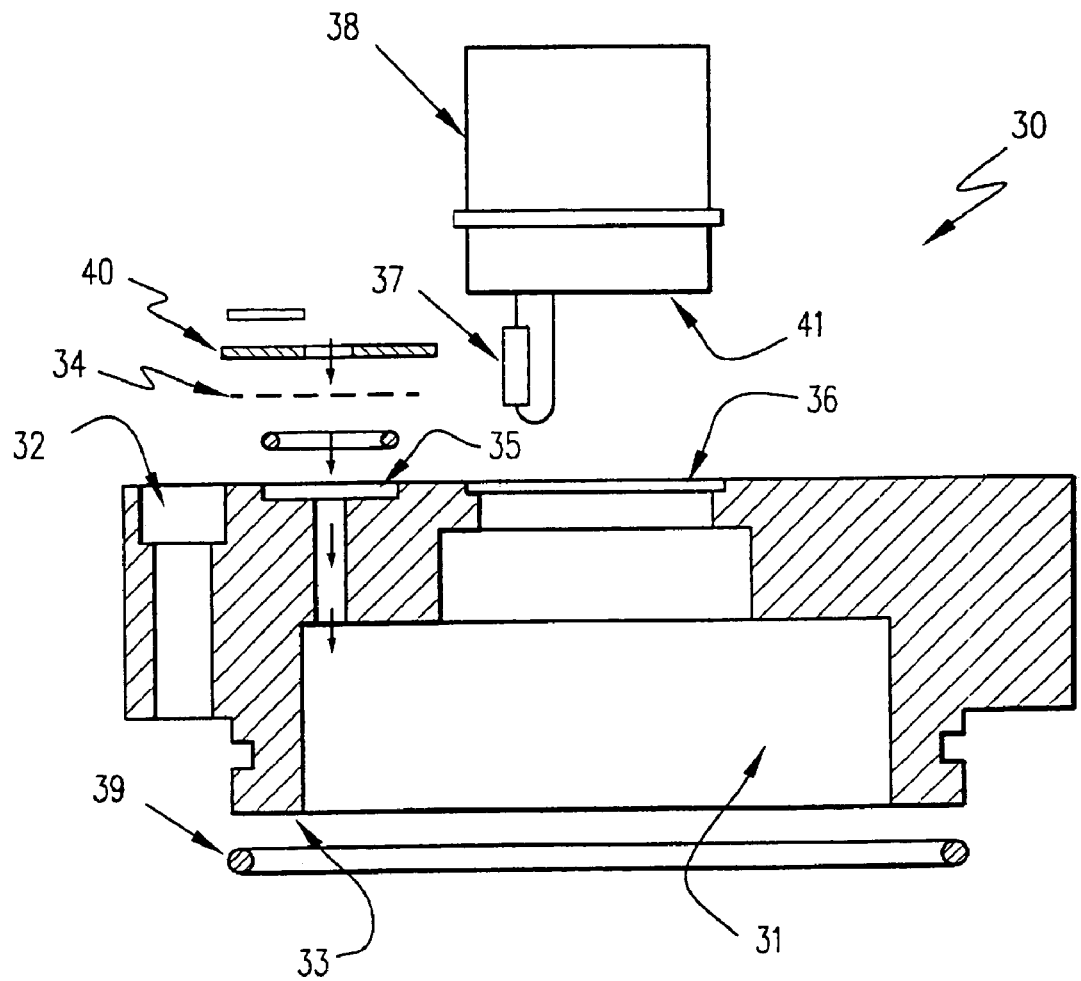
FIG. 3 is a cross-sectional view of a cover assembly of the micro-fuel cell sensor body of FIG. 2.

FIG. 3 illustrates a cover member 30 for covering the sensor body 11 in an airtight manner. Cover member 30 includes a slot 31 having an upper end 36 and a lower end 33. The cover member 30 sealingly covers the sensor body 20 as illustrated in FIG. 2. Cover member 30 further includes a vent 35 for permitting oxygen from atmospheric air to enter the second cavity of sensor 10 through slot 31. At least one fastener may be used to secure the cover member 30 to the sensor body 11 as illustrated in FIG. 2. The third gas permeable membrane 34 separates vent 35 from the atmospheric air. A perforated vent cover plate 40 overlies and protects the third membrane. A connector member 38 having an end portion 41 is disposed in an airtight manner in the upper portion 36 of slot 31. The connector 38 includes a resistor 37 which projects out into the upper portion 36 of slot 31. Sensor leads 8-1 and 8-2 connected on one side to the first electrode 4-1 and 4-2, respectively, terminate in connector 38. The output of the sensor 10 is represented by the potential difference between sensor leads 8-1 and 8-2 through resistor 37.

Micro fuel cell gas sensors can be utilized in several fluid systems to measure several gasses dissolved in liquids or combined in a gas or vapor stream. Typically, these devices contain thin polymeric membranes that are sensitive to temperature and pressure variations. These membranes have gas permeation characteristics that selectively allow certain either dissolved in a liquid or in a gaseous or vapor stream to pass into the fuel cell. In one example, thin polymeric membranes allow gasses dissolved in dielectric oil to pass through to a micro fuel cell.

These membranes plastically deform over time with temperature cycles. This permanent deformation affects the membrane permeability, which in turn affects the accuracy of the sensor. Further, the thin membranes are sensitive to pressure variations. These membranes are robust for positive pressure, as long as the membranes are supported by a metal disc, but rupture under negative pressure. This membrane rupture leads to failure of the sensor device.

The exemplary sensor 10, as embodied by the invention, is utilized to measure hydrogen gas dissolved in dielectric oil in an electrical transformer. This application of the sensor and any of the dimensions and values provided herein are merely exemplary of the sensor as embodied by the invention and are not meant to limit the invention mentioned herein. Other applications, dimensions, and values are within the scope of the invention.

In the exemplary embodiment, a micro fuel cell gas sensor 10 comprises sensing element comprising first and second gas diffusing electrodes 4-1 and 4-2 spaced from one another by a fuel-cell spacer 5 having an acidic electrolyte disposed between the first and second electrodes 4-1 and 4-2, and first and second gas permeable membrane 1 and 7.

The first and second gas diffusion electrodes 4-1 and 4-2 of the exemplary embodiment are identical and comprise platinum on carbon. Other materials suitable for electrode material are utilized in other embodiments to facilitate an electrochemical reaction specific to each monitoring process. These other materials can include, for example, Gold, Palladium, Palladium-Platinum, Ruthenium, Iridium, Osmium, Rhodium, or Tantalum. The electrodes are utilized with the fuel cell spacer 5 to monitor the gas.

The fuel cell spacer 5 comprises an acidic electrolyte interconnecting said first and second electrodes 4-1 and 4-2. This electrolyte takes part in the process of the electrochemical oxidation of a dissolved gas at said first electrode 4-1 and the electrochemical reduction of oxygen at said second electrode 4-2. In the exemplary embodiment, the oxidation reaction at the first electrode 4-1 comprises hydrogen, and the reduction reaction at the second electrode 4-2 comprises oxygen from ambient air. Although the electrochemical oxidation in this embodiment comprises hydrogen gas, other gasses comprising at least one of carbon monoxide, acetylene, ethylene, methane, and ethane can be oxidized at the first electrode 4-1. As in this embodiment, oxygen from the ambient air is reduced at the second electrode to measure the partial pressure of those gasses respectively.

Figure 4:
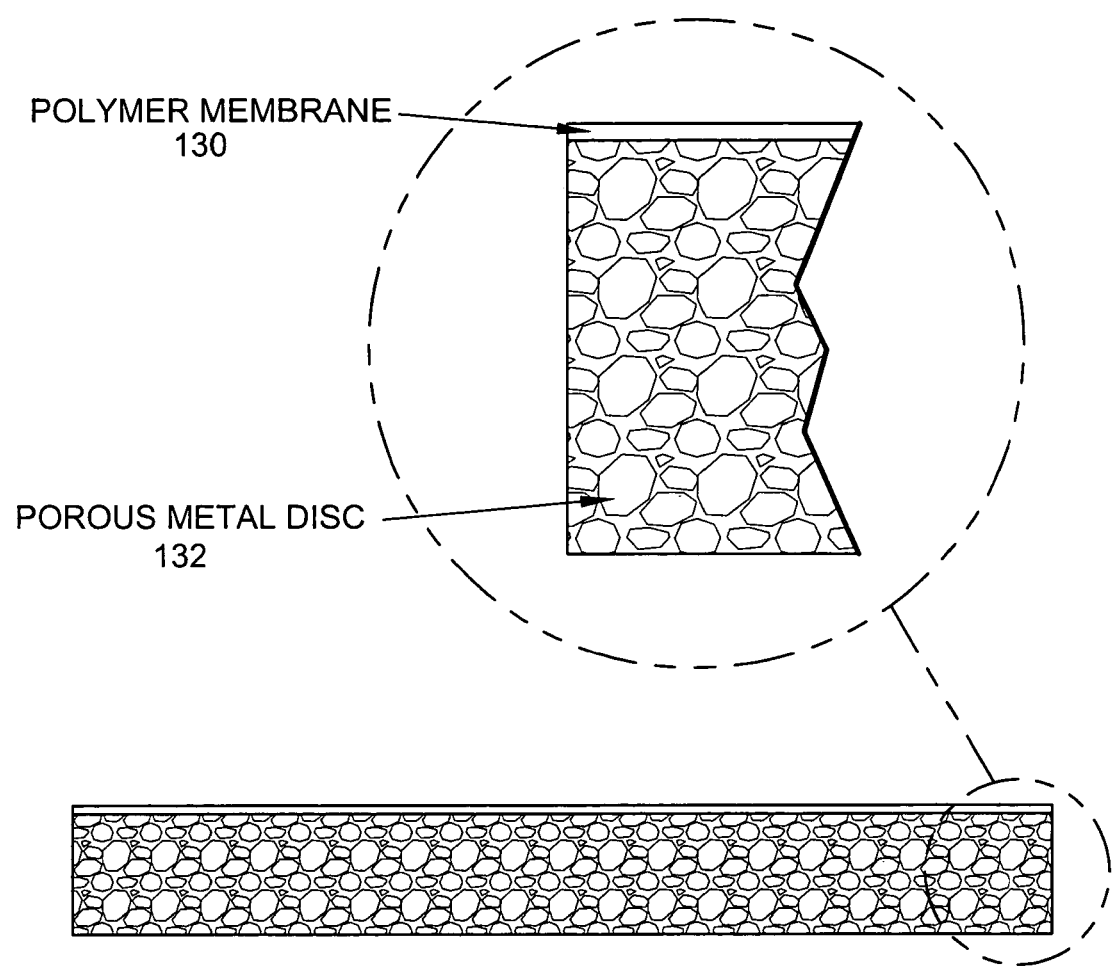
FIG. 4 illustrates a polymer film on a porous metal substrate.

The gas permeable membrane 1 of this embodiment comprises a polymer 130 laminated on a porous metal disc 132 as shown in FIG. 4. The membrane 1 is impervious to oil, thus allowing a gas dissolved in dielectric oil to pass through the membrane 1 but not the oil. The gas permeation rate through the laminated membranes 1 is less than the rate of the electrochemical reaction occurring at the first electrode 4-1.

The polymer 130 in the exemplary embodiment comprises at least one of Polytetrafluoroethylene (PTFE), Perfluorinated Ethylene-Propylene Copolymer (FEP), Perfluoroalkoxy PTFE (PFA), Polyvinylidene fluoride (PVDF), Polyvinyl Chloride (PVC), Polyimide, Polyethylene (PE), Polyether Ester Ketone (PEEK), Polycarbonate (PC) and Polyurethane. Selection of the polymer depends upon the permeability of the gas desired to be measured and the solution system. The polymer thickness in this embodiment ranges from about 25 micron to about 250 micron (about 1 mil to about 10 mil).

The laminated membrane 1 in this embodiment further comprises a porous metal disc 132 that supports the polymer film 130 under both positive and negative pressure. The metal disc 132 further comprises at least one of stainless steel, high nickel and nickel-copper alloys, bronze, and titanium, alloys thereof, and combinations thereof.

In the exemplary embodiment, the polymer membrane is applied to a porous metal disc at an elevated temperature and at constant pressure. The porous metal disc is manufactured by a sintering process. Both the method of applying the polymer film and the method of manufacture of the metal disc are chosen to ensure that the gas permeability of the polymer film is the same after lamination as it was before lamination. Methods of applying polymer films to metal and of manufacturing porous metal discs, other than those disclosed in the exemplary embodiment can also be utilized to produce the laminated gas membrane disclosed herein.

The dimension of the pores of the metal disc 132 are less than or equal to about one-half of the polymer 130 thickness. A ratio of pore size to film 130 thickness in this range prevents the membrane perforation during the lamination process and allows for good adherence of the polymer to the metal disc 132. The pores of the metal disc 132 are much larger than the gas molecules to be analyzed by the sensor, thus allowing the gas to pass through the membrane at about the same diffusion rate as a polymer only membrane.

While various embodiments are described herein, it will be appreciated from the specification that various combinations of elements, variations or improvements therein may be made by those skilled in the art, and are within the scope of the invention.

What is claimed is:

1. A micro-fuel cell sensor for sensing a dissolved gas in a fluid stream, the sensor comprising:
    a housing;
    a sensing element comprising first and second gas diffusing electrodes spaced from one another, said sensing element disposed in said housing;
    a fuel-cell spacer having an acidic electrolyte disposed between said first and second electrodes;
    a first gas permeable membrane separating said first electrode from oil in the dissolved gas and enabling the gas to diffuse therethrough, said first gas permeable membrane is laminated to, affixed to and supported by a porous substrate, and said first gas permeable membrane being spaced from said first electrode enabling gas diffused through said first membrane to contact said first electrode, and
    a second gas permeable membrane separating said second electrode from atmospheric air and defining a second cavity therewith isolated from said first cavity.

2. The sensor of claim 1, wherein said first and second electrodes are identical and comprise at least one of Platinum on carbon, Gold, Palladium, Palladium-platinum, Ruthenium, Iridium, Osmium, Rhodium, or Tantalum.

3. The sensor of claim 1, wherein the acidic electrolyte interconnecting said first and second electrodes facilitate the electrochemical oxidation of a dissolved gas at said first electrode and electrochemical reduction at said second electrode.

4. The sensor of claim 3, wherein the electrochemical oxidation at said first electrode of a gas, wherein said gas comprises at least one of hydrogen, carbon monoxide, acetylene, ethylene, methane, and ethane and electrochemical reduction at said second electrode, wherein said gas at second electrode comprises oxygen from the ambient air.

5. The sensor of claim 1, wherein the porous substrate is a porous metal disc.

6. The sensor of claim 5, wherein the first gas permeable membrane is impervious to oil.

7. The sensor of claim 5, wherein the first gas permeable membrane is vacuum resistant.

8. The sensor of claim 5, wherein the gas permeation rate through the laminated membrane is less than the rate of the electrochemical gas sensing reaction occurring in the sensor.

9. The sensor of claim 5, rein the polymer comprises at least one of Polytetrafluoroethylene, Perfluorinated Ethylene-Propylene Copolymer, Perfluoroalkoxy Polytetrafluoroethylene, Polyvinylidene Fluoride, Polyvinyl Chloride, Polyimide, Polyethylene, Polyether Ester Ketone, Polycarbonate and Polyurethane.

10. The sensor of claim 5, wherein the polymer has a thickness in a range from about 25 micron (1 mil) to about 250 micron (10 mil).

11. The sensor of claim 5, wherein the metal disc supports the polymer film under positive and negative pressure.

12. The sensor of claim 11, wherein the metal disc comprises at least one of stainless steel, high nickel and nickel-copper alloys, bronze, and titanium.

13. The sensor of claim 11, wherein the metal disc comprises pores.

14. The sensor of claim 11, wherein the dimension of the pores of the metal disc is less than or equal to about one-half of the polymer film thickness.

15. The sensor of claim 11, wherein the dimension of the pores of the metal disc are much larger than the gas molecules to be analyzed by the sensor.

16. The sensor of claim 1, wherein the second gas permeable membrane comprises a polymer.

17. An apparatus for determining dissolved gasses in oil, the apparatus comprising:
   a housing;
   a micro-fuel cell sensor disposed in said housing;
   a cover member;
   said sensor comprising:
      a sensing element comprising first and second gas diffusing electrodes spaced from one another, said sensing element disposed in said housing;
      a fuel-cell spacer having an acidic electrolyte disposed between said first and second electrodes;
      a first gas permeable polymer membrane separating said first electrode from the oil with dissolved gas and enabling gas dissolved in oil to diffuse therethrough, said first gas permeable polymer membrane is laminated to, affixed to and supported by a porous sintered metallic substrate, and said first gas permeable polymer membrane being spaced from said first electrode enabling gas diffused through said first gas permeable polymer membrane to contact said first electrode, and
      a second gas permeable membrane separating said second electrode from atmospheric air and defining a second cavity therewith isolated from said first cavity.

18. The sensor of claim 17, wherein said cover member further comprises:
   a connector for providing an electrical connection to said sensor; and
   a third gas permeable membrane disposed in one of said cover member and said housing for receiving atmospheric air.

19. In a sensor having a housing, a sensing element comprising first and second gas diffusing electrodes spaced from one another, said sensing element disposed in said housing and comprising;
   a fuel-cell spacer having an acidic electrolyte disposed between said first and second electrodes, wherein said electrodes comprise platinum on carbon;
   a first gas permeable membrane separating said first electrode from the oil with dissolved gas and enabling gas dissolved in oil to diffuse therethrough, said first gas permeable membrane being spaced from said first electrode enabling gas diffused through said first membrane to contact said first electrode, wherein said gas permeable membrane is impervious to oil and further wherein a gas permeation rate through the first gas permeable membrane is less than a rate of an electrochemical gas sensing reaction occurring in the sensor;
   said first gas permeable membrane including:
      a polymer film consisting of at least one of Polytetrafluoroethylene, Perfluorinated Ethylene-Propylene Copolymer, Perfluoroalkoxy Polytetrafluoroethylene, Polyvinylidene fluoride, Polyvinyl Chloride, Polyimide, Polyethylene, Polyether Ester Ketone, Polycarbonate and Polyurethane; and further the polymer film has a thickness in a range from about 25 micron (1 mil) to about 250 micron (10 mil); wherein the polymer film is laminated to a porous sintered metallic disc to support the polymer film such that the polymer film remains affixed to the sintered metallic disc under positive and negative pressures and pores in the porous sintered metallic disc have diameters less than or equal to about one-half of the polymer film thickness; and wherein a dimension of the pores of the sintered metallic disc are larger than the gas molecules to be analyzed by the sensor.

20. A micro-fuel cell sensor for sensing a dissolved gas in a fluid stream, the sensor comprising:
   a housing;
   a sensing element comprising first and second gas diffusing electrodes spaced from one another, said sensing element disposed in said housing;
   a fuel-cell spacer having an acidic electrolyte disposed between said first and second electrodes;
   a first gas permeable polymer membrane separating said first electrode from oil in the dissolved gas and permeable to gas, said first gas permeable polymer membrane is laminated to, secured to an supported by a porous sintered metallic disc substrate, and said first gas permeable polymer membrane is spaced from said first electrode, and
   a second gas permeable membrane separating said second electrode from atmospheric air and defining a second cavity therewith isolated from said first cavity.

* * * * *